United States Patent [19]

Mims

[11] 4,076,948

[45] Feb. 28, 1978

[54] PROCESS FOR TREATMENT OF ADIPIC ACID MOTHER LIQUOR

[75] Inventor: Samuel S. Mims, Odessa, Tex.

[73] Assignee: El Paso Products Company, Odessa, Tex.

[21] Appl. No.: 766,476

[22] Filed: Oct. 10, 1968

[51] Int. Cl.$^2$ .................. C07C 69/34; C07C 69/44; C07C 69/48

[52] U.S. Cl. ........................... 560/191; 560/204; 260/531 R; 260/537 R; 260/537 P

[58] Field of Search ............... 260/485 S, 485, 533 C, 260/531, 537 D

[56] References Cited

U.S. PATENT DOCUMENTS

| | | | |
|---|---|---|---|
| 2,824,122 | 2/1958 | Kuceski | 260/485 |
| 2,968,674 | 1/1961 | Franke et al. | 260/485 R |
| 3,329,712 | 4/1967 | Danly et al. | 260/533 |

FOREIGN PATENT DOCUMENTS

| | | |
|---|---|---|
| 705,578 | 3/1941 | Germany. |
| 933,714 | 8/1963 | United Kingdom. |

Primary Examiner—Jane S. Myers
Attorney, Agent, or Firm—DePaoli & O'Brien

[57] ABSTRACT

Treatment of aqueous nitric acid solutions resulting from the nitric acid oxidation of cyclohexanol and/or cyclohexanone in the presence of metal compound oxidation catalysts for recovery of the valuable components contained therein, which comprises adding an alcohol to the aqueous nitric acid solution to esterify the acids present, contacting the resultant alcoholic mixture with a water-immiscible solvent, separating layers into an aqueous phase and an organic phase, treating the aqueous phase to recover the nitric acid and catalyst components and treating the organic phase to recover the acid derivatives.

11 Claims, 1 Drawing Figure

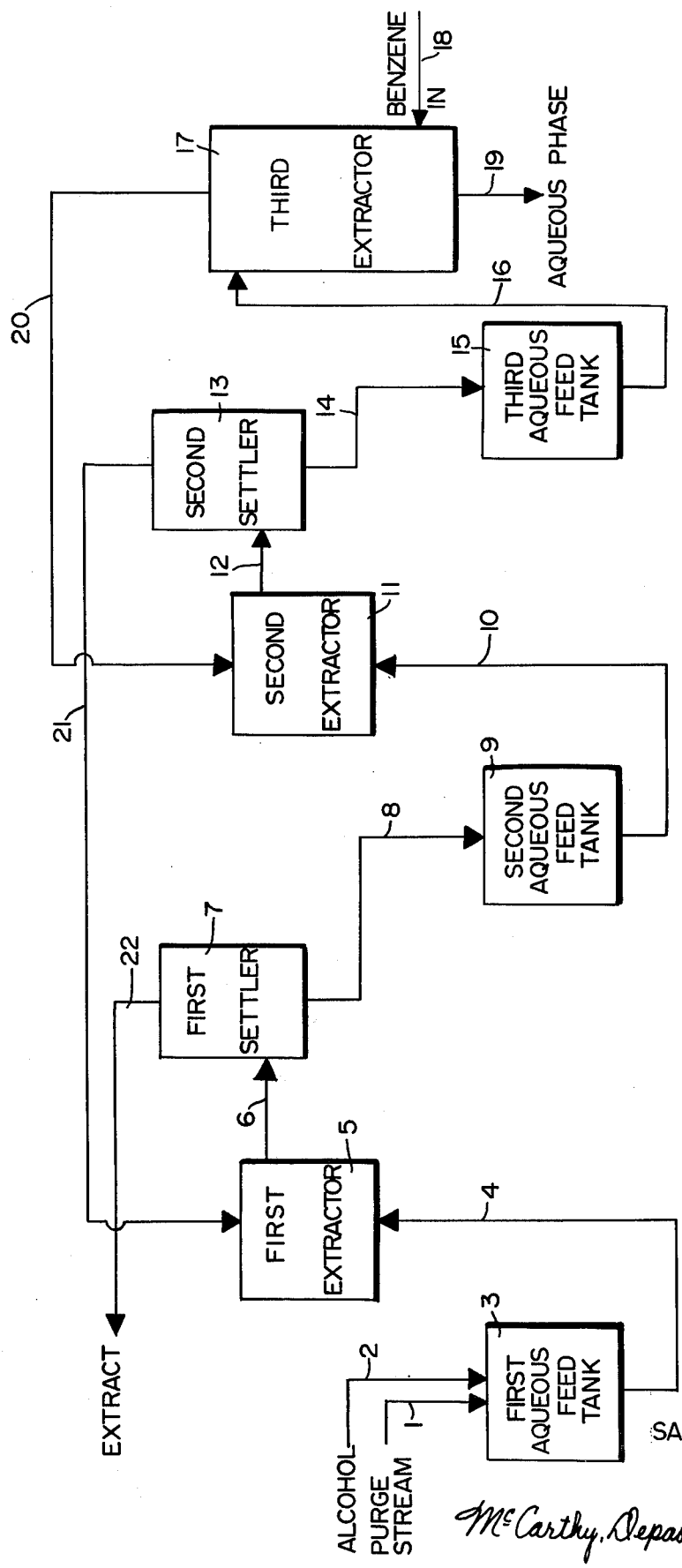

PROCESS FOR TREATMENT OF ADIPIC ACID MOTHER LIQUOR

BACKGROUND OF THE INVENTION

1. Field of the Invention

This invention relates to a process for the recovery of organic acids and other useful products such as nitric acid and catalysts contained in aqueous nitric acid solutions resulting from the oxidation of cyclohexanol and/or cyclohexanone to produce adipic acid.

2. Description of the Prior Art

The art is well aware of processes for producing useful acids, such as adipic acid, by oxidizing naphthenes, cycloaliphatic ketones or cycloaliphatic alcohols with nitric acid in the presence of metal compound oxidation catalysts. Such processes in general involve heating specific materials such as cyclohexane, cyclohexanol and/or cyclohexanone in nitric acid at about 40° to 140° C., generally utilizing nitric acid of about 20 to 90 percent strength, to produce a resulting oxidation mixture comprising the adipic acid together with small amounts of other dicarboxylic acids in admixture with the unused nitric acid and catalyst components. Generally, the art subsequently recovers a substantial amount of the desirable product, adipic acid, by cooling the solution and filtering off the crystallized adipic acid. Such processes for producing the adipic acid are known, for example, in the prior art from U.S. Pat. Nos. 2,791,566; 2,840,607; 3,338,959; 2,971,010; 2,439,513; and 2,557,282.

Adipic acid, of course, is an important intermediate for the production of nylon by subsequent copolymerization with hexamethylenediamine to produce a polyamide capable of being spun into a fiber having a number of desirable characteristics.

In the processes known to the art, however, very little attention has been paid to recovery of the valuable materials which can be further utilized by recycling the same to the nitric acid oxidation process such as unused nitric acid and catalytic components. Moreover, the other organic acids contained therein have usually been treated as waste materials.

In the process for nitric acid oxidation of cyclohexanol and/or cyclohexanone, significant amounts of succinic acid and glutaric acid are formed as byproducts in admixture with the adipic acid. Various well known schemes of crystallization, concentration and further crystallization have been used heretofore in industry to attempt separation thereof and usually a substantial amount of the adipic acid can be removed by these procedures. Ultimately, however, a mother liquor is obtained from these operations which contains succinic acid, glutaric acid, and a small amount of adipic acid in such proportions that further concentration and crystallization steps will yield only mixtures of these dibasic acids. In addition, as a result of the removal of the adipic acid by crystallization and removal of the water and nitric acid by volatilization, the concentration of the metal catalyst in this final mother liquor becomes relatively high. Hence, loss of these materials, particularly the catalytic components, provides a distinct economic disadvantage as the relatively high proportion of valuable and reusable products is lost.

It is clear, therefore, that a distinct need remains in the art for processes by which this nitric acid oxidation mother liquor may be processed so as to recover the valuable components contained therein in an economic and efficient manner.

SUMMARY OF THE INVENTION

It is accordingly, one object of the present invention to provide a process for the removal of organic dibasic acids and other valuable components contained in nitric acid oxidation mother liquors of cyclohexanol and/or cyclohexanone.

A further object of the invention is to provide a method for the recovery of such materials in reusable form uncontaminated by the presence of the other materials.

A still further object is to provide a process by which these materials may be recovered without the addition thereto of materials which would tend to accumulate in recycle streams and to eliminate costly crystallization and filtration steps.

Other objects and advantages of the present invention will become apparent as the description thereof proceeds.

In satisfaction of the foregoing objects and advantages, the process of the present invention provides a procedure for the removal of organic acids and recovery of catalytic components contained in the dilute aqueous nitric acid purge stream resulting from the nitric acid oxidation of cyclohexanol and/or cyclohexanone in the presence of metal compound oxidation catalysts, which comprises adding an alcohol to the aqueous nitric acid solution to esterify the acids present, contacting the resultant alcoholic mixture with a water immiscible solvent, separating the resulting layers into an aqueous phase and an organic phase, and processing the organic phase and processing the aqueous phase to recover the desired products.

Also within the scope of this invention are procedures whereby the aqueous phase may be processed to yield an alcohol fraction, a water fraction, and a residue comprising nitric acid and the metal compound oxidation catalyst which may be recycled to the nitric acid oxidation system and processes for treating the organic phase to yield a water immiscible solvent phase and the individual esters formed during the esterification step. In addition, procedures are provided for treatment of the esters to obtain other forms of the acids.

BRIEF DESCRIPTION OF THE DRAWING

Reference is now made to the accompanying drawing which illustrates, in diagram form, one procedure by which the process of the present invention can be conducted.

DESCRIPTION OF THE PREFERRED EMBODIMENTS

As pointed out above, the process of this invention provides a procedure for the removal and recovery of valuable organic acids, nitric acid and catalytic components contained in the mother liquor resulting from the nitric acid oxidation of cyclohexanol and/or cyclohexanone in the presence of metal compound oxidation catalysts. The process also provides means whereby the metal compound oxidation catalyst as well as the nitric acid contained therein can be recovered in a form suitable for recycling in the original oxidation process.

In the oxidation of cyclohexanol and/or cyclohexanone in the presence of metal compound oxidation catalysts with nitric acid, the resulting acid solution is generally processed for recovery of the bulk of the desirable adipic acid contained therein. However, the remaining mother liquor also contains a substantial amount of other organic acids as well as the catalytic components and some nitric acid as to be sufficiently valuable to be processed to recover the valuable materials contained therein. This mother liquor will generally be found to contain the following components in the percent indicated based on the total weight of the mother liquor.

| Component | Amount |
| --- | --- |
| Succinic acid | 3–10% |
| Glutaric acid | 8–35% |
| Adipic acid | 3–6% |
| Nitric acid | 6–20% |
| Catalyst | 1–3% |
| Water | Balance |

Thus, the mother liquor, when operating on a commercial scale, contains a substantial amount of materials which are sufficiently valuable to be recovered in order to conduct the original oxidation process in an efficient and economical manner.

The catalytic components contained in this mixture are the catalysts usually employed in this process and generally comprise copper, vanadium, etc., their compounds and/or other catalytic reagents known to the art for use in the nitric acid oxidation process.

Briefly, the process of this invention entails the addition of an alcohol to the final adipic acid mother liquor or purge stream obtained from the oxidation process. The solution is then contacted with a suitable water-immiscible solvent so that a combination reaction and extraction takes place and, surprisingly, nearly complete removal of the dibasic acids from the aqueous phase into the non-aqueous phase is easily effected. The dibasic acids are in the form of their diester derivatives in the non-aqueous or organic phase. This non-aqueous phase can be distilled or otherwise processed to recover the solvent and the remaining ester mixture processed further by one or more of several suitable techniques such as fractional distillation, transesterification, crystallization or hydrolysis to yield useful products. The aqueous phase may be processed as desired but is preferably distilled to recover the excess alcohol and the water to yield the catalyst compounds contained in the remaining nitric acid solution, the latter being ideal for reuse in the nitric acid oxidation.

As described above, the final adipic acid mother liquor or purge stream containing the components mentioned is treated with an alcohol, preferably by use of an alcohol in about equal volume, or at least in a sufficient amount to esterify the acids contained therein. The alcohols employed are preferably the lower alkyl alcohols, including methanol, ethanol, n-propyl alcohol, isopropyl alcohol, n-butyl alcohol, sec.-butyl alcohol, and the like. In general, alcohols containing about 1 to 5 carbon atoms, preferably primary alcohols, may be employed to advantage in the present process. Methanol represents an especially preferred alcohol for use in this process, however, because of its low cost, high reactivity, and the greater ease of fractionation of its esters. Under other conditions, however, other alcohols may of course be employed.

The alcohol may be added at room temperatures or any temperature ranging from about 25° C. up to about the boiling point of the alcohol employed in the process. In general, as the alcohol reacts with the acids contained in the solution to form the dialkyl esters thereof, the higher the temperature employed, the faster will be the reaction so that it is generally preferred to conduct this reaction at a slightly elevated temperature in order to obtain maximum esterification in the shortest time possible. A preferred temperature range is about 55° C. up to the boiling point of the alochol employed, as at room temperature for example, several hours are often required to reach these maximum values whereas under conditions of heat this time is reduced to a few minutes.

After addition of the alcohol to the solution and formation of the esters, a substantially equal volume of a water immiscible solvent is added to the mixture and it is allowed to stand at about ambient temperature for sufficient time to obtain separation of layers. Immiscible solvents which have been found to be particularly suitable for this aspect of the process, include the aromatic hydrocarbons, polarizable materials and polar solvents as opposed to materials which do not shows these characteristics. In general, the aromatic hydrocarbons, such as benzene, toluene, xylene, ethyl benzene, halogenated aliphatic and aromatic hydrocarbons such as chloroform, chlorobenzene, dichlorobenzene, etc. are most suitable. Also, in certain instances, water-immiscible materials such as pelargonic acid and the like may also be used. In general, any material which is substantially water-immiscible and which will extract a good portion of the esters may be employed in the aspect of the process. Of these several extractants, benzene is an especially suitable immiscible solvent as it is readily available, chemically inert, easily recovered, and provides good and consistent results.

After the addition of the water-immiscible solvent, the two layers are allowed to layer out and the aqueous phase and organic phase separated for further processing.

The aqueous phase and organic phase can be processed in any desirable manner to recover the valuable products contained therein. The aqueous phase contains the excess alcohol, water, the nitric acid and catalytic components, as well as a very small amount of the organic acids which were not esterified. This aqueous layer is most suitably processed by subjecting to fractional distillation to remove alcohol and water fractions and recycling the remaining residue containing nitric acid concentrated in catalytic components to the nitric acid oxidation process. However, any other suitable processing technique may be employed.

The organic phase will be found to contain the water-immiscible solvent and the esters, both as mono- and diesters and may also be processed as desired. A very suitable processing technique is to subject the organic phase to distillation by fractionation so as to separate the water-immiscible solvent as one fraction and the several esters contained therein as a second fraction. This ester mixture is in itself valuable to prepare high molecular weight esters useful as plasticizers for polyvinyl chlorides. However, the crude esters may be further fractionated to yield in pure form the diester of succinic acid, the diester of glutaric acid and the diester of adipic acid. These individual ester compounds can then be hydrolyzed either separately or in a mixture to yield the pure acids or can be processed in other ways to yield useful products.

The process has been described above with respect to conducting the process of this invention by the batch method. However, the process can also be conducted in a continuous manner using the combination reaction and extraction procedure. Explanation of the process conducted in a continuous manner is best made by reference to the drawing accompanying this application.

In the drawing, it will be seen that a series of extractors and settlers are employed in combination with aqueous feed tanks so as to provide a system for the continuous extraction of the esterified purge stream.

In the illustration, the first and second extractors are stirred vessels or pots in order to obtain good admixture and thus good ester extraction. The third extractor is a packed column operated so that the aqueous phase is maintained as a continuous phase. Hold-up times of the aqueous phase should be maintained in this extractor to provide for complete reaction. Hold-up times of about ¼ to 1 hour, preferably one-half hour are satisfactory. The aqueous feed tanks are of a size such that there is also sufficient hold-up time, i.e., about one hour, in each tank in order to obtain good admixture and complete reaction. The extractors and feed tanks are generally maintained at an elevated temperature as described hereinabove and preferably at about above 55° C. Referring now to the drawing specifically, a purge stream 1 from an adipic acid mother liquor source is fed into the first aqueous feed tank 3 together with alcohol by line 2. The alcohol and the purge stream are preferably introduced into the first aqueous feed tank in about equal volumes. This solution is then fed continuously to the series of extractors and settlers and feed vessels while an appropriate volume of benzene or other water-immiscible solvent is fed by line 18 to the opposite end of the series of extractors, settlers and feed vessels so that the entire system operates in a countercurrent fashion. Thus, in the first aqueous feed tank 3, the alcohol and purge stream components react to esterify the acids and the mixture is then passed by line 4 to the first extractor 5 where it is contacted with extractant coming from second settler 13 by line 21. This mixture passes to first settler 7 where layers are separated and crude extract removed continuously via line 22.

In the meantime, the aqueous phase from first settler 7 is passed by line 8 to second feed tank 9, then by line 10 to second extractor 11 where it is mixed with further extractant coming from the third extractor 17 by line 20. The mixture is then passed via line 12 to second settler 13 for layer separation, the extract being removed by line 21 and sent to first extractor 5, and the aqueous phase passing by line 14 to the third feed tank 15 and then by line 16 to the third extractor 17. Fresh water-immiscible solvent such as benzene is added to the third extractor 17 by line 18 so as to maintain sufficient extractant present to remove all the esters and this overhead is forwarded to second extractor 11 by line 20. The aqueous phase is removed by line 19 for further processing as desired.

Thus, by utilizing this method in a continuous manner, the purge stream can be continuously processed to continuously recover a crude extract from line 22 containing the esters formed and the aqueous phase from line 19 containing the alcohol excess, water, nitric acid and catalyst components. Then these streams may be further processed as desired as set forth above.

The process of this invention thus provides a number of advantages over processes of the art which have been used in an attempt to recover these valuable components. Hence, in the present process, the removal of nitric acid and water from the mixture is not required as, for example, by volatilization, as this is a hazardous step when carried to dryness. Further, distillation of the high boiling dibasic acids is not required; there is no necessity for the addition of non-volatile acids or other inorganic materials which would accumulate in recycle stream; costly crystallization and filtration steps are eliminated and the aqueous and organic phases are obtained in uncontaminated form.

As opposed to prior art techniques, the present process is simple and economical but still affords the simultaneous recovery of dibasic acids as well as of the metallic catalysts contained in the mixture. Moreover, the materials are recovered in highly useful form, the dibasic acids being recovered as diester derivatives useful as a mixture or easily processed by further means to yield individual compounds such as the individual esters, by hydrolysis to recover the acids; by transesterification to produce more useful, particularly high molecular weight, esters. The metal catalysts are recovered as a concentrated solution in nitric acid and thus, in an ideal form for reuse in the cyclohexanol/cyclohexanone nitric acid oxidation reaction.

The following examples further exemplify certain embodiments of the process but the invention is not to be considered as limited thereto.

In these examples, parts are by weight unless otherwise indicated.

EXAMPLE 1

This example illustrates the ineffectiveness of extraction and of esterification when done separately.

Final adipic acid mother liquor containing 4% succinic acid, 32% glutaric acid, 5% adipic acid, 16% nitric acid, and 2% catalysts was shaken with an equal volume of benzene periodically during a 24-hour period. The benzene layer was removed and the aqueous layer analyzed. The analysis indicated that the aqueous layer remained essentially unchanged in composition.

Final adipic acid mother liquor, with the composition given above, was mixed with an equal volume of methanol. This yielded a homogeneous solution which was allowed to stand for three weeks. There was no formation of an immiscible layer, and hence the dibasic acids could not be removed.

EXAMPLE II

This example shows the effectiveness of the combination reaction and extraction of the subject process.

Final adipic acid mother liquor, with the composition given in Example I, was mixed with an equal volume of methanol. This solution was fed continuously to the series of extractors, settlers and feed vessels shown in the process diagram on the accompanying drawing. For each volume fed of this solution, an equal volume of benzene was fed to the opposite end of the series of extractors, settlers, and feed vessels so that the entire system operated in a countercurrent fashion.

The first and second extractors were stirred pots with a twenty-minute hold-up time in each pot. The third extractor was a packed column operated so that the aqueous phase was the continuous phase. Hold-up time of the aqueous phase was about thirty minutes. The aqueous feed tanks were sized so that there was at least an hour's hold-up time in each feed tank. The extractors and feed tanks were maintained at 58° C.

The crude extract recovered from this operation was found on analysis to contain 2.24% dimethyl succinate, 18.57% dimethyl glutarate, and 2.46% dimethyl adipate in benzene solution. Distillation of this extract yielded benzene for reuse in the extraction, together with a mixed dimethyl ester fraction.

The crude aqueous phase from the extraction was distilled to remove the excess methanol. After this operation, analysis indicated that the aqueous phase contained 0.29% succinic acid, 0.60% glutaric acid, and 0.01% adipic acid. Concentration of this solution by removal of water under vacuum yielded a solution containing 32.7% nitric acid, 6% catalysts, and about 4% organic acids. This last solution can be reused in the nitric acid oxidation of cyclohexanol/cyclohexanone to adipic acid.

EXAMPLE III

This example shows the effectiveness of various immiscible solvents in the subject process.

A solution containing 8% adipic acid, 20% nitric acid, and 2% catalysts was prepared. One volume of this solution was then mixed with one volume of methanol and one volume of an immiscible solvent. The resulting mixture was then allowed to stand at ambient temperature for 24 hours. The water-immiscible layer was then separated and analyzed for adipate esters. Results are tabulated below.

TABLE I

| | Ester Content of Extract, Wt.% | |
|---|---|---|
| Immiscible Solvent | Dimethyl Adipate | Monomethyl Adipate |
| Benzene | 6.0% | .07% |
| Toluene | 7.0% | Trace |
| Xylene | 6.0% | Trace |
| Ethylbenzene | 6.0% | .05% |
| Chloroform | 7.0% | 0% |
| o-Dichlorobenzene | 5.0% | 0% |
| Pelargonic Acid | 5.0% | 0% |
| Hexane | 1.5% | 0% |
| Cyclohexane | 1.5% | 0% |

This table indicates that solvents characterized by aromaticity, polarizability, and polarity are particularly effective in this process whereas the hexane and cyclohexane do not provide as effective results.

EXAMPLE IV

This example shows the effect of time and temperature in the subject process.

A. Solutions were prepared as in Example III using benzene as the immiscible solvent. The immiscible layer was separated after varying time periods at ambient temperatures and analyzed for adipate esters. Results are tabulated below.

TABLE II

| | Ester Content of Extract, Wt. % | |
|---|---|---|
| Time In Contact | Dimethyl Adipate | Monomethyl Adipate |
| 1 Minute | .05% | .08% |
| 15 Minutes | .75% | .44% |
| 30 Minutes | .78% | .43% |
| 1 Hour | 1.68% | .45% |
| 2 Hours | 3.20% | .48% |
| 3 Hours | 4.40% | .37% |
| 19 Hours | 4.97% | .12% |

B. Solutions consisting of one volume of the final adipic acid mother liquor, described in Example I, and one volume of methanol were prepared. These were allowed to stand for varying periods of time after which they were shaken with one volume of benzene. The benzene layer was separated at once and analyzed. Results are given in the table below.

TABLE III

| Time before Extraction | Ester Content of Extract, Wt.% | | | | | |
|---|---|---|---|---|---|---|
| | Dimethyl | | | Monomethyl | | |
| | Succinate | Gluterate | Adipate | Succinate | Glutarate | Adipate |
| 1 Hour | .6 | 7.5 | 1.4 | .07 | 1.33 | .28 |
| 20 Hours | 1.3 | 10.2 | 2.1 | 0 | .47 | .04 |
| 2 Days | 1.3 | 9.9 | 2.0 | 0 | .88 | .07 |
| 3 Days | 1.2 | 9.8 | 1.9 | 0 | .59 | .11 |
| 6 Days | 1.4 | 11.4 | 2.1 | — | — | — |

C. Extractions were carried out exactly as those above, except that the final adipic acid mother liquor-methanol solutions were heated under reflux (65° C) for varying periods of time prior to extraction with benzene. The results are tabulated below.

TABLE IV

| Time Heated Before Extraction | Ester Content of Extract, Wt.% | | | | | |
|---|---|---|---|---|---|---|
| | Dimethyl | | | Monomethyl | | |
| | Succinate | Glutarate | Adipate | Succinate | Glutarate | Adipate |
| 30 Min. | 1.2 | 10.1 | 2.0 | 0 | .27 | .04 |
| 1 Hour | 1.2 | 10.2 | 2.0 | 0 | .24 | .03 |
| 2 Hours | 1.2 | 10.6 | 2.1 | 0 | .29 | .03 |
| 3 Hours | 1.2 | 10.6 | 1.9 | .03 | .31 | .10 |

Examination of data in the above tables shows that a maximum value of the ester content of the extract is reached. At room temperature several hours are required to affect this maximum separation; under mild heating this time is reduced to several minutes.

EXAMPLE V

This example illustrates a three-stage extraction rather than the countercurrent extraction of Example II.

Final adipic acid mother liquor containing 3% succinic acid, 12% glutaric acid, 5% adipic acid, 7% nitric acid, and 1.4% catalysts was mixed with an equal volume of methanol. This solution was fed continuously to the series of extractors, settlers and feed vessels shown in the diagram of the drawing. For each two volumes of this solution fed, one volume of benzene was fed to each of the three extractors. The extracts leaving the three settlers were collected separately (and were not fed to another extractor as indicated on the figure). Other than this feeding of benzene and collecting of extracts, all process variables were as described in the discussion of the drawing and in Example II.

The extracts analyzed as follows:

TABLE V

| | Weight Percent in Benzene | | | | | |
|---|---|---|---|---|---|---|
| | Dimethyl | | | Monomethyl | | |
| | Succinate | Glutarate | Adipate | Succinate | Glutarate | Adipate |
| 1st Stage | 1.34 | 6.48 | 4.21 | .10 | .59 | .43 |
| 2nd Stage | .93 | 3.50 | 1.71 | .08 | .25 | .15 |
| 3rd Stage | .85 | 2.61 | 1.03 | .08 | .12 | .06 |

On analysis, the crude raffinate after methanol removal, was found to contain 0.71% succinic acid, 0.90% glutaric acid, and 0.20% adipic acid. Concentration yielded a solution containing 29% nitric acid, 5% catalysts, and 8% organic acids.

EXAMPLE VI

This example illustrates the use of alcohols other than methanol in the process of this invention.

A solution containing 8% adipic acid, 20% nitric acid, and 2% catalysts was prepared. One volume of this solution was mixed with one volume of the alcohol. After standing 30 hours, one volume of benzene was added. After periodic shaking for 6 hours, the layers were separated. Results of the analysis of the benzene layer are tabulated below.

TABLE VI

| Alcohol Used | Ester Content of Extract, Wt. % | |
|---|---|---|
| | Diester | Monoester |
| Methanol | 7% | 0.1% |
| Ethanol | 4% | 1.4% |
| n-Propyl Alcohol | 3% | .6% |
| i-Propyl Alcohol | 0.5% | 1.0% |
| sec-Butyl Alcohol | 0.5% | 1.3% |
| t-Butyl Alcohol | 0% | 0% |

The crude mixed ester fraction, obtained after benzene removal, may be distilled in a simple vacuum distillation to yield a refined mixed ester fraction. This refined fraction has been used to prepare high molecular weight esters valuable as plasticizers for polyvinyl chloride. Alternatively, the crude ester fraction has also been distilled to yield pure dimethyl succinate, dimethyl glutarate, and dimethyl adipate. These compounds can be hydrolyzed by known methods to yield the pure acids or can be processed other ways to yield useful products.

The essential steps in the subject process are the mixing of the alcohol with the aqueous acid mixture, the continuous or periodic contacting of the resulting solution with an immiscible solvent, followed by the separation of the immiscible layers and the processing of the two solutions obtained to yield useful materials. These steps may be carried out under a variety of conditions using a wide variety of equipment.

The invention has been described hereinabove with reference to certain preferred embodiments thereof. However, it is to be understood that the invention is not to be limited thereto as obvious modifications thereof will be apparent to those skilled in the art.

What is claimed is:

1. In a process for the treatment of the mother liquor resulting from the nitric acid oxidation of cyclohexanol and/or cyclohexanone and the recovery of valuable components therefrom, which mother liquor contains a mixture of aliphatic dibasic acids, nitric acid and metal catalyst values, the improved process which comprises:
   a. contacting said mother liquor with a water-miscible lower alkyl alcohol at a temperature of from 25° C. to the boiling point of the alcohol used and in a sufficient amount to esterify at least a portion of the aliphatic dibasic acids present and form an esterifying mixture;
   b. contacting said esterifying mixture with a sufficient amount of a substantially water-immiscible organic solvent to extract the esters formed into said organic solvent, said organic solvent being selected from the group consisting of aromatic hydrocarbons, halogenated aliphatic hydrocarbons, halogenated aromatic hydrocarbons and mixtures thereof;
   c. continuing contact of said esterifying mixture and said organic solvent until at least a portion of the esters formed are partitioned into an organic phase comprising the esters dissolved in said organic solvent and there is formed said organic phase and an aqueous phase containing water, nitric acid, metal catalyst values, any excess alcohol and any unesterified organic acids;
   d. separating said organic phase and said aqueous phase;
   e. distilling said organic phase to remove the organic solvent and recover the lower alkyl esters of the aliphatic dibasic acids;
   f. distilling the aqueous phase to remove any excess lower alkyl alcohol and excess water; and
   g. recovering a residue which comprises an aqueous nitric acid solution containing metal catalyst values.

2. A process according to claim 1 wherein the mother liquor contains succinic acid, glutaric acid, adipic acid, metallic catalyst components and nitric acid.

3. A process according to claim 2 wherein the lower alkyl alcohol is a primary straight or branch chain alcohol having one to about five carbon atoms and the water-immiscible solvent is selected from the group consisting of benzene, toluene, xylene, ethylbenzene, chloroform and ortho-dichlorobenzene.

4. A process according to claim 3 wherein the mixture or organic esters is fractionally distilled to separately recover dialkyl succinate, dialkyl glutarate and dialkyl adipate.

5. In a continuous process for the treatment of the mother liquor which results from the nitric acid oxidation of cyclohexanol and/or cyclohexanone and the recovery of valuable components therefrom, which mother liquor contains a mixture of aliphatic dibasic acids, nitric acid and metal catalyst values, the improved process which comprises:
   a. continuously contacting said mother liquor with a water-miscible lower alkyl alcohol at a temperature of from 25° C. to the boiling point of the alcohol used and in a sufficient amount to esterify at least a portion of the dibasic acids present and form an esterifying mixture;
   b. continuously contacting said esterifying mixture in a countercurrent manner with a sufficient amount of a substantially water-immiscible organic solvent to extract the esters formed into said organic solvent; said organic solvent being selected from the group consisting of aromatic hydrocarbons, halogenated aliphatic hydrocarbons, halogenated aromatic hydrocarbons and mixtures thereof, said countercurrent contact being carried out by passing said esterifying mixture into at least one extractor and passing said organic solvent into at least one said extractor countercurrent to said esterifying mixture;
   c. continuing said countercurrent contact for a sufficient time to extract at least a portion of the esters formed into said organic solvent;
   d. removing the resulting mixture from the said at least one extractor, passing to at least one settler and permitting the mixture to layer out to form an organic phase and an aqueous phase, said organic phase containing esters of the aliphatic dibasic acids dissolved in said organic solvent and said aqueous phase containing water, nitric acid, metal catalyst values, any excess alcohol and any unesterified aliphatic dibasic acids;
   e. separating said organic phase and said aqueous phase and passing said organic phase and said aqueous phase to separate distillation stages;
   f. distilling said organic phase to remove organic solvent for recycle to at least one of said extractors and recovering a mixture of dialkyl esters of the aliphatic dibasic acids;

g. distilling said aqueous phase to remove any excess lower alkyl alcohol and excess water and provide a residue which comprises an aqueous nitric acid solution containing metal catalyst values and any unesterified organic acids;

h. recycling said residue to the nitric acid oxidation of cyclohexanol and/or cyclohexanone.

6. A process according to claim 5 wherein the mother liquor contains succinic acid, glutaric acid, adipic acid, and nitric acid.

7. A process according to claim 6 wherein the esterifying alcohol is a primary straight or branch chain alcohol having one to about five carbon atoms and the water-immiscible solvent is selected from the group consisting of benzene, toluene, xylene, ethylbenzene, chloroform and ortho-dichlorobenzene.

8. A process according to claim 7 wherein the mixture of dialkyl esters of aliphatic dibasic acids recovered in step (e) is fractionally distilled to separately recover dialkyl succinate. dialkyl glutarate and dialkyl adipate.

9. A process according to claim 7 wherein the alcohol is methanol, the water-immiscible solvent is benzene, and these materials are employed in a volume equal to the volume of liquid being treated in the esterification and extraction step.

10. In a process for the treatment of the mother liquor resulting from the nitric acid oxidation of cyclohexanol and/or cyclohexanone and the recovery of valuable components therefrom, which mother liquor contains a mixture of aliphatic dibasic acids, nitric acid and metal catalyst values, the improved process which comprises:

a. contacting said mother liquor with a water-miscible lower alkyl alcohol at a temperature of from 25° C. to the boiling point of the alcohol used and in a sufficient amount to esterify at least a portion of the aliphatic dibasic acids present and form an esterifying mixture;

b. contacting said esterifying mixture with a sufficient amount of a substantially water-immiscible organic solvent to extract the esters formed into said organic solvent, said organic solvent being selected from the group consisting of aromatic hydrocarbons, halogenated aliphatic hydrocarbons and halogenated aromatic hydrocarbons;

c. continuing contact of said esterifying mixture and said organic solvent until at least a portion of the esters formed are partitioned into an organic phase comprising the esters dissolved in said organic solvent and there is formed said organic phase and an aqueous phase containing water, nitric acid, metal catalyst values, and excess alcohol and any unesterified organic acids;

d. separating said organic phase and said aqueous phase;

e. distilling said organic phase to remove the organic solvent and recover the lower alkyl esters of the aliphatic dibasic acids;

f. distilling the aqueous phase to remove any excess lower alkyl alcohol and excess water;

g. recovering a residue which comprises an aqueous nitric acid solution containing metal catalyst values; and h. recycling the recovered residue of nitric acid solution containing metal catalyst values to the nitric acid oxidation of cyclohexanol and/or cyclohexanone.

11. In a process for the treatment of the mother liquor resulting from the nitric acid oxidation of cyclohexanol and/or cyclohexanone and the recovery of valuable components therefrom, which mother liquor is a dilute aqueous nitric acid stream containing metal oxidation catalysts, a mixture of adipic, succinic and glutaric acids and from 6 to 20 weight percent nitric acid, the improved process which comprises:

a. contacting said mother liquor with methanol at a temperature of from 25° C to the boiling point of the alcohol and in an amount sufficient to esterify said acids present and form an esterifying mixture of methyl esters;

b. contacting said esterifying mixture with a sufficient amount of benzene solvent to extract the esters formed into said solvent;

c. continuing contact of said esterifying mixture and benzene until at least a portion of the methyl esters formed are partitioned into an organic phase comprising the esters dissolved in benzene and there is formed said organic phase and an aqueous phase containing water, nitric acid, metal catalyst values, any excess alcohol and any unesterified organic acids;

d. separating said organic phase and said aqueous phase;

e. distilling said organic phase to remove benzene and recover the methyl esters of said acids;

f. distilling the aqueous phase to remove any excess methanol and excess water; and g. recovering a residue which comprises an aqueous nitric acid solution containing metal catalyst values.

* * * * *

UNITED STATES PATENT OFFICE
CERTIFICATE OF CORRECTION

Patent No. 4,076,948　　　　　　　Dated February 28, 1978

Inventor(s)　　Samuel S. Mims

It is certified that error appears in the above-identified patent and that said Letters Patent are hereby corrected as shown below:

The term of this patent subsequent to

November 15, 1994, has been disclaimed.

Signed and Sealed this

Second Day of May 1978

[SEAL]

Attest:

RUTH C. MASON
Attesting Officer

LUTRELLE F. PARKER
Acting Commissioner of Patents and Trademarks